United States Patent
Labbe et al.

(10) Patent No.: US 9,616,240 B2
(45) Date of Patent: Apr. 11, 2017

(54) SYSTEMS AND METHODS FOR FAST DISCHARGE IN PACING CIRCUITS DURING RF INTERFERENCE

(71) Applicant: Pacesetter, Inc., Sunnyvale, CA (US)

(72) Inventors: Eric Labbe, Sunnyvale, CA (US); Will Heng Zhang Lui, Venture, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 14/850,501

(22) Filed: Sep. 10, 2015

(65) Prior Publication Data
US 2017/0072204 A1 Mar. 16, 2017

(51) Int. Cl.
*A61N 1/37* (2006.01)
*A61N 1/05* (2006.01)
*A61N 1/08* (2006.01)

(52) U.S. Cl.
CPC .......... *A61N 1/3718* (2013.01); *A61N 1/056* (2013.01); *A61N 1/08* (2013.01)

(58) Field of Classification Search
CPC ......... A61N 1/3718; A61N 1/056; A61N 1/08
USPC .............................................. 607/9
See application file for complete search history.

(56) References Cited

U.S. PATENT DOCUMENTS

| | | | |
|---|---|---|---|
| 7,389,140 B1* | 6/2008 | Kroll | A61N 1/36114 607/9 |
| 2002/0095187 A1* | 7/2002 | Thompson | A61N 1/37 607/9 |

* cited by examiner

*Primary Examiner* — Paula J Stice
(74) *Attorney, Agent, or Firm* — Theresa A. Raymer

(57) ABSTRACT

The present disclosure provides a cardiac pacing system. The cardiac pacing system includes a right atrial ring electrode, a right atrial tip electrode, a right ventricle ring electrode, and a pacing integrated circuit (IC) including a first pace output node electrically coupled to the right atrial ring electrode, a pace return node electrically coupled to the right atrial tip electrode, and a second pace output node electrically coupled to the right ventricle ring electrode, wherein the pacing IC has a fast discharge configuration that facilitates reducing or eliminating a DC rectification current generated from RF interference during a fast discharge phase.

16 Claims, 8 Drawing Sheets

SYSTEMS AND METHODS FOR FAST DISCHARGE IN PACING CIRCUITS DURING RF INTERFERENCE

FIELD OF THE DISCLOSURE

The present disclosure relates generally to cardiac stimulation systems, and more particularly to pacing circuits configured to prevent generation of a large DC rectification current from RF interference during a fast discharge phase.

BACKGROUND ART

Heart failure (HF) is a debilitating, end-stage disease in which abnormal function of the heart leads to inadequate blood flow to fulfill the needs of the body's tissues. Typically, the heart loses propulsive power because the cardiac muscle loses capacity to stretch and contract. Often, the ventricles do not adequately fill with blood between heartbeats and the valves regulating blood flow may become leaky, allowing regurgitation or backflow of blood. The impairment of arterial circulation deprives vital organs of oxygen and nutrients. Fatigue, weakness, and inability to carry out daily tasks may result.

Not all HF patients suffer debilitating symptoms immediately. Some may live actively for years. Yet, with few exceptions, the disease is relentlessly progressive. As HF progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output.

Current standard treatment for HF is typically centered around medical treatment using ACE inhibitors, diuretics, and digitalis. It has also been demonstrated that aerobic exercise may improve exercise tolerance, improve quality of life, and decrease symptoms. Cardiac surgery has also been performed on a small percentage of patients with particular etiologies. Although advances in pharmacological therapy have significantly improved the survival rate and quality of life of patients, some HF patients are refractory to drug therapy, have a poor prognosis and limited exercise tolerance. In recent years cardiac pacing has emerged as an effective treatment for many patients with drug-refractory HF.

Notably, magnetic resonance imaging (MRI) scanners produce relatively large radio-frequency (RF) fields during operation. These RF fields may induce a corresponding RF voltage at device lead electrodes across feedthrough capacitors of an implantable cardiac device (ICD) or pacemaker in a patient undergoing MRI scanning. If the RF voltage is sufficiently high, it may result in unintended myocardial stimulation due to a DC current that results from rectification of the induced RF voltage.

This DC rectification current may be particularly large during a fast discharge phase of pacing capacitors for electrodes of the ICD/pacemaker. This is referred to as a cross-channel rectification current, as fast discharge on one channel/electrode generates a DC rectification current on another channel/electrode. The cross-channel rectification current may, for example, cause undesirable atrial fibrillation. Accordingly, it would be desirable to provide patients with an ICD/pacemaker that facilitates preventing unintended myocardial stimulation when subjected to large RF interference.

BRIEF SUMMARY OF THE DISCLOSURE

In one embodiment, the present disclosure is directed to a cardiac pacing system. The cardiac pacing system includes a right atrial ring electrode, a right atrial tip electrode, a right ventricle ring electrode, and a pacing integrated circuit (IC) including a first pace output node electrically coupled to the right atrial ring electrode, a pace return node electrically coupled to the right atrial tip electrode, and a second pace output node electrically coupled to the right ventricle ring electrode, wherein the pacing IC has a fast discharge configuration that facilitates reducing or eliminating a DC rectification current generated from RF interference during a fast discharge phase.

In another embodiment, the present disclosure is directed to a pacing integrated circuit (IC) for use in a cardiac pacing system. The pacing IC includes a first pacing output node configured to be electrically coupled to a right atrial ring electrode, a pace return node configured to be electrically coupled to a right atrial tip electrode, and a second pace output node configured to be electrically coupled to a right ventricle ring electrode, wherein the pacing IC has a fast discharge configuration that facilitates reducing or eliminating a DC rectification current generated from RF interference during a fast discharge phase.

In another embodiment, the present disclosure is directed to a method of assembling a cardiac stimulation system. The method includes electrically coupling a right atrial ring electrode to a first pace output node of a pacing integrated circuit (IC), electrically coupling a right atrial tip electrode to a pace return node of the pacing IC, and electrically coupling a right ventricle ring electrode to a second pace output node of the pacing IC, wherein the pacing IC has a fast discharge configuration that facilitates reducing or eliminating a DC rectification current generated from RF interference during a fast discharge phase.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides patients with an MRI-compatible pacing device that allows full-body MRI scans to be performed on pacing-dependent patients. The pacing device has a semi-floating or floating fast discharge configuration that prevents generation of a large DC rectification current during RF interference. The systems and methods described herein also enable MRI-compatible devices to include VOO and/or DOO modes because cross-channel rectification is no longer an issue.

Figure 1A:
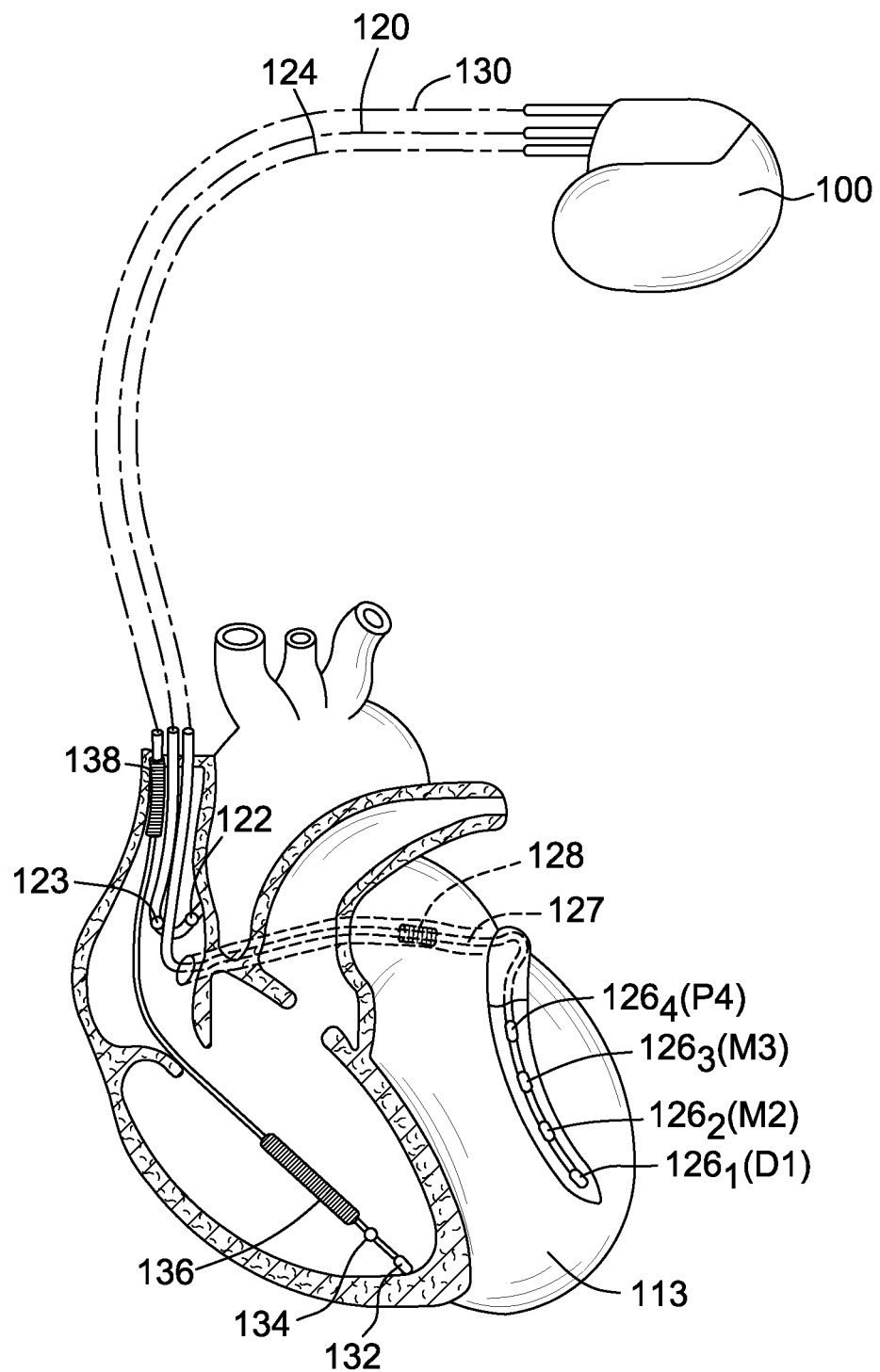
FIG. 1A is a simplified, partly cutaway view illustrating an implantable stimulation device in electrical communication with at least three leads implanted into a patient's heart for delivering multi-chamber stimulation and shock therapy and sensing cardiac activity.
Figure 1B:
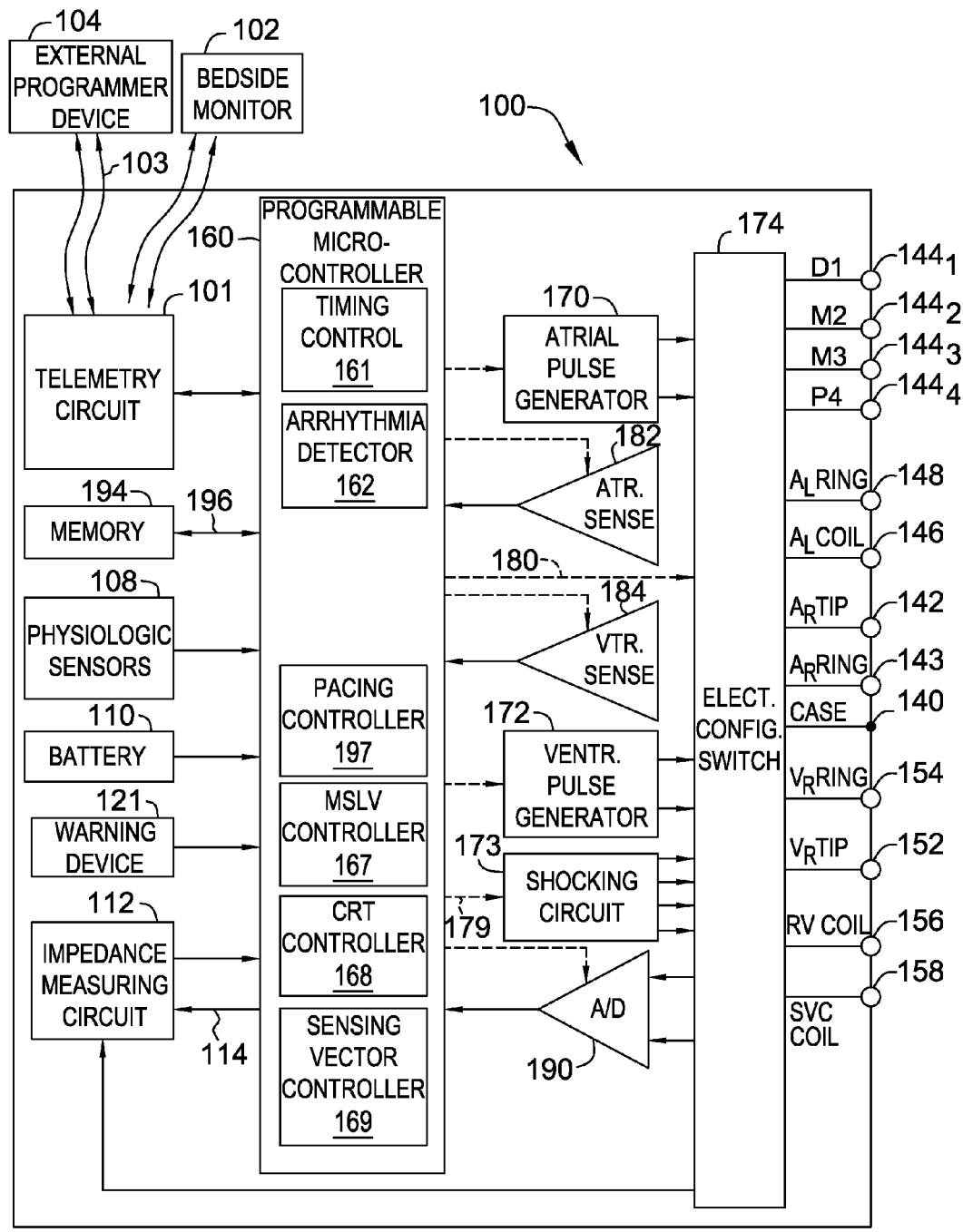
FIG. 1B is a functional block diagram of the multi-chamber implantable stimulation device of FIG. 1A, illustrating the basic elements that provide pacing stimulation, cardioversion, and defibrillation in four chambers of the heart.

With reference to FIGS. 1A and 1B, a description of an example pacemaker/implantable cardioverter-defibrillator (ICD) 100 will now be provided. FIG. 1A is a simplified block diagram of pacemaker/ICD 100, which is a dual-chamber stimulation device capable of treating both fast and slow arrhythmias with stimulation therapy, including cardioversion, defibrillation, and pacing stimulation, including multi-site left ventricular (MSLV) pacing. To provide atrial chamber pacing stimulation and sensing, pacemaker/ICD 100 is shown in electrical communication with a heart 113 by way of a right atrial (RA) lead 120 having an atrial tip electrode 122 and an atrial ring electrode 123 implanted in the atrial appendage. Pacemaker/ICD 100 is also in electrical communication with heart 113 by way of a right ventricular (RV) lead 130 having, in this embodiment, a ventricular tip electrode 132, a RV ring electrode 134, a RV coil electrode 136, and a superior vena cava (SVC) coil electrode 138. Typically, RV lead 130 is transvenously inserted into the heart so as to place RV coil electrode 136 in the RV apex, and SVC coil electrode 138 in the superior vena cava. Accordingly, RV lead 130 is capable of receiving cardiac signals, and delivering stimulation in the form of pacing and shock therapy to the right ventricle (also referred to as the RV chamber).

To sense left atrial and ventricular cardiac signals and to provide left chamber pacing therapy, pacemaker/ICD 100 is coupled to a multi-pole left ventricular (LV) lead 124 designed for placement in the "CS region" for positioning a distal electrode adjacent to the left ventricle and/or additional electrode(s) adjacent to the left atrium (also referred to as the LA chamber). As used herein, the phrase "CS region" refers to the venous vasculature of the left ventricle, including any portion of the coronary sinus (CS), great cardiac vein, left marginal vein, left posterior ventricular vein, middle cardiac vein, small cardiac vein, and/or any other cardiac vein accessible by the CS. Accordingly, an example LV lead 124 is designed to receive atrial and ventricular cardiac signals and to deliver left ventricular pacing therapy using a set of four LV electrodes $126_1$, $126_2$, $126_3$, and $126_4$ (thereby providing a quadra-pole lead), left atrial pacing therapy using at least a LA ring electrode 127, and shocking therapy using at least a LA coil electrode 128. In some embodiments, LV lead 124 includes LV electrodes $126_1$, $126_2$, $126_3$, and $126_4$, but does not include LA ring and coil electrodes 127 and 128. Such a lead can be, e.g., the Quartet™ left ventricular pacing lead developed by St. Jude Medical Inc. (headquartered in St. Paul, Minn.), which includes four pacing electrodes on the left ventricular lead—enabling up to ten pacing configurations LV electrode $126_1$ is shown as being the most "distal" LV electrode (with relation to how far the electrode is from where LV lead 124 connects to pacemaker/ICD 100). For example LV electrode $126_1$ may be located at the apex of the left ventricle. LV electrode $126_4$ is shown as being the most "proximal" LV electrode. For example LV electrode $126_4$ may be located at the base of the left ventricle. LV electrodes $126_2$ and $126_3$ are shown as being "middle" LV electrodes, between distal and proximal LV electrodes $126_1$ and $126_4$. Accordingly, the four LV electrodes $126_1$, $126_2$, $126_3$, and $126_4$ can be referred to respectively as electrodes D1, M2, M3 and P4 (where "D" stands for "distal", "M" stands for "middle", and "P" stands from "proximal", and the numbers are arranged from most distal to most proximal). It is also possible that more or fewer LV electrodes are provided. However, for much of the remaining discussion, it will be assumed that the multi-pole LV lead 124 includes four LV electrodes $126_1$, $126_2$, $126_3$, and $126_4$ (i.e., LV electrodes D1, M2, M3 and P4, respectively).

LV electrodes $126_1$, $126_2$, $126_3$, and $126_4$ can be used to provide various pacing vectors and sensing vectors. Some of the vectors are intraventricular LV vectors (vectors between two LV electrodes); whereas others are interventricular vectors (e.g., vectors between an LV electrode and RV coil electrode 136). Below is a list of exemplary vectors that can be used for pacing and/or sensing using LV electrodes D1, M2, M3 and P4 with and without RV coil electrode 136. In the following list, the first electrode in each row (i.e., the electrode to the left of the arrow) is assumed to be connected as the cathode, and the second electrode in each row (i.e., the electrode to the right of the arrow) is assumed to be connected as the anode, but that need not be the case, especially where neither electrode is a coil.

D1→RV coil
M2→RV coil
M3→RV coil
P4→RV coil
D1→M2
D1→P4
M2→P4
M3→M2
M3→P4
P4→M2

Alternative and/or additional vectors, other than those listed above, can be used for pacing and/or sensing. Although only three leads are shown in FIG. 1A, it should also be understood that additional leads (with one or more pacing, sensing, and/or shocking electrodes) might be used and/or additional electrodes might be provided on the leads already shown, such as additional electrodes on the RV or LV lead. It is also possible that less than three leads be used.

A simplified block diagram of internal components of pacemaker/ICD 100 is shown in FIG. 1B. While a particular pacemaker/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. A housing 140 for pacemaker/ICD 100, shown schematically in FIG. 1B, is often referred to as the "can", "case" or "case electrode" and may be programmably selected to act as the return electrode for all "unipolar" modes. Housing 140 may further be used as a return electrode alone or in combination with one or more of coil electrodes, 128, 136 and 138 for shocking purposes. Housing 140 further includes a connector (not shown) having a plurality of terminals, 142, 143, $144_1$-$144_4$, 146, 148, 152, 154, 156 and 158 (shown schematically and, for convenience, the names of the electrodes to which they are connected are shown next to the terminals). As such, to achieve RA sensing and pacing, the connector includes at least an RA tip terminal ($A_R$ TIP) 142 adapted for connection to the atrial tip electrode 122 and an RA ring ($A_R$ RING) electrode 143 adapted for connection to RA ring electrode 123. To achieve left chamber sensing, pacing and shocking, the connector includes an LV tip terminal $144_1$ adapted for connection to the D1 electrode and additional LV electrode terminals $144_2$, $144_3$ and $144_4$ terminals adapted for connection to the M2, M3 and P4 electrodes of quadra-pole LV lead 124.

The connector also includes an LA ring terminal ($A_L$ RING) 148 and an LA shocking terminal ($A_L$ COIL) 146, which are adapted for connection to LA ring electrode 127 and the LA coil ($A_L$ COIL) electrode 128, respectively. To support right chamber sensing, pacing and shocking, the connector further includes an RV tip terminal ($V_R$ TIP) 152, an RV ring terminal ($V_R$ RING) 154, an RV shocking terminal ($V_R$ COIL) 156, and an SVC shocking terminal (SVC COIL) 158, which are adapted for connection to RV tip electrode 132, RV ring electrode 134, RV coil electrode 136, and SVC coil electrode 138, respectively.

At the core of pacemaker/ICD 100 is a programmable microcontroller 160, which controls the various modes of stimulation therapy. As is well known in the art, microcontroller 160 (also referred to herein as a control unit or controller) typically includes a microprocessor, or equivalent control circuitry, designed specifically for controlling the delivery of stimulation therapy and may further include RAM or ROM memory, logic and timing circuitry, state machine circuitry, and I/O circuitry. Typically, microcontroller 160 includes the ability to process or monitor input signals (data) as controlled by a program code stored in a designated block of memory.

As shown in FIG. 1B, an atrial pulse generator 170 and a ventricular pulse generator 172 generate pacing stimulation pulses for delivery by RA lead 120, RV lead 130, and/or LV lead 124 via an electrode configuration switch 174. Microcontroller 160 includes timing control circuitry 161 to control the timing of the stimulation pulses, including, but not limited to, pacing rate, atrio-ventricular (AV) delay, interatrial conduction (AA) delay, interventricular conduction (VV) delay and/or intraventricular delay (e.g., LV1-LV2 delay). Timing control circuitry 161 can also keep track of timing of refractory periods, blanking intervals, noise detection windows, evoked response detection windows, alert intervals, marker channel timing, etc.

Microcontroller 160 further includes an arrhythmia detector 162 that can be utilized by the stimulation device 100 for determining desirable times to administer various therapies. Additional components of the microcontroller include a MSLV controller 167 to control the actual delivery of MSLV pacing and a cardiac resynchronization therapy (CRT) controller 168 to control CRT, which can be performed in conjunction with MSLV pacing.

Microcontroller 160 is also shown as including a sensing vector controller 169 that can be used, e.g., to control the electrode configuration switch 174 (e.g., via control signals 180) to selectively connect specific electrode(s) to sensing circuits 182 or 184 as a cathode or an anode, to achieve the various sensing vectors that are used to obtain IEGMs in accordance with embodiments described herein. Where multiple sensing vectors are being used to obtain a plurality of IEGMs indicative of cardiac electrical activity at a plurality of ventricular regions, sensing circuit 184 may include multiple channels (e.g., duplicate circuitry) to enable sensing of more than one ventricular IEGM signal at the same time, and/or sensing circuit 184 may use time divisional multiplexing to sense more than one ventricular IEGM signal.

Depending upon the implementation, the various components of the microcontroller may be implemented as separate software modules or the modules may be combined to permit a single module to perform multiple functions. For example, the MSLV controller and the CRT controller 168 can be combined. In addition, although shown as being components of the microcontroller, some or all of these components may be implemented separately from the microcontroller, using application specific integrated circuits (ASICs) or the like.

Switch 174 includes a plurality of switches for connecting the desired electrodes to the appropriate I/O circuits, thereby providing complete electrode programmability. Accordingly, switch 174, in response to a control signal 180 from microcontroller 160, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 182 and ventricular sensing circuits 184 may also be selectively coupled to RA lead 120, LV lead 124, and RV lead 130, through switch 174 for detecting the presence of cardiac activity in each of the four chambers of the heart. Accordingly, the atrial (ATR. SENSE) and ventricular (VTR. SENSE) sensing circuits, 182 and 184, may include dedicated sense amplifiers, multiplexed amplifiers or shared amplifiers. Switch 174 determines the "sensing polarity" of the cardiac signal by selectively closing the appropriate switches, as is also known in the art. In this way, a clinician may program the sensing polarity independent of the stimulation polarity. Each sensing circuit, 182 and 184, preferably employs one or more low power, precision amplifiers with programmable gain and/or automatic gain control, bandpass filtering, and a threshold detection circuit, as known in the art, to selectively sense the cardiac signal of interest. The automatic gain control enables pacemaker/ICD 100 to deal effectively with the difficult problem of sensing the low amplitude signal characteristics of atrial or ventricular fibrillation. The outputs of the atrial and ventricular sensing circuits, 182 and 184, are connected to the microcontroller 160 which, in turn, are able to trigger or inhibit the atrial and ventricular pulse generators, 170 and 172, respectively, in a demand fashion in response to the absence or presence of cardiac activity in the appropriate chambers of the heart.

Cardiac signals are applied to the inputs of an analog-to-digital (A/D) data acquisition system 190. Data acquisition system 190 is configured to acquire intracardiac electrogram signals, convert the raw analog data into a digital signal, and store the digital signals for later processing and/or telemetric transmission to an external programmer 104 or a bedside monitor or personal advisory module (PAM) 102. Data acquisition system 190 is coupled to RA lead 120, LV lead 124, and RV lead 130 through switch 174 to sample cardiac signals across any pair of desired electrodes. Microcontroller 160 is further coupled to a memory 194 by a suitable data/address bus 196, wherein the programmable operating parameters used by microcontroller 160 are stored and modified, as required, in order to customize the operation of pacemaker/ICD 100 to suit the needs of a particular patient.

Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each pacing and shocking pulse to be delivered to the patient's heart within each respective tier of therapy. Other pacing parameters include base rate, rest rate and circadian base rate.

Advantageously, the operating parameters of implantable pacemaker/ICD 100 may be non-invasively programmed into memory 194 through a telemetry circuit 101 in telemetric communication with external device 104 or bedside monitor 102, such as a programmer, transtelephonic transceiver, or a diagnostic system analyzer. The telemetry circuit 101 is activated by the microcontroller by a control signal 106. Telemetry circuit 101 advantageously allows intracardiac electrograms and status information relating to the operation of pacemaker/ICD 100 (as contained in microcontroller 160 or memory 194) to be sent to external device 104 and/or bedside monitor 102 through an established communication link 103. An internal warning device 121 (also referred to as a patient alert) may be provided for generating perceptible warning signals to the patient via vibration, voltage or other methods.

Pacemaker/ICD 100 further includes an accelerometer or other physiologic sensor 108, commonly referred to as a "rate-responsive" sensor because it is typically used to adjust pacing stimulation rate according to the exercise state of the patient. Pacemaker/ICD additionally includes a battery 110 that provides operating power to the circuits shown in FIG. 1B. As further shown in FIG. 1B, pacemaker/ICD 100 is shown as having an impedance measuring circuit 112, which is enabled by the microcontroller 160 via a control signal 114. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. Impedance measuring circuit 112 is advantageously coupled to switch 174 so that any desired electrode may be used.

In the case where pacemaker/ICD 100 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, microcontroller 160 further controls a shocking circuit 173 by way of a control signal 179. Shocking circuit 173 generates shocking pulses of low (up to 0.1 joules), moderate (0.1-10 joules) or high energy (11 to 40 joules or more), as controlled by the microcontroller 160. Such shocking pulses are applied to the heart of the patient through at least two shocking electrodes, and as shown in this embodiment, selected from LA coil electrode 128, RV coil electrode 136, and/or SVC coil electrode 138. Housing 140 may act as an active electrode in combination with RV coil electrode 136, or as part of a split electrical vector using SVC coil electrode 138 or LA coil electrode 128 (i.e., using RV coil electrode 136 as a common electrode). In this embodiment, microcontroller 160 further includes a pacing controller 197. Pacing controller 197 controls pacemaker/ICD 100 during a fast discharge phase, as described herein.

Pacemaker/ICD 100 is provided as an example. One or ordinary skill in the art would understand that embodiments described herein can be used with alternative types of implantable devices. Accordingly, embodiments described herein should not be limited to use only with the above described device.

In at least some known pacing circuits, during a fast discharge phase, following or preceding a pace pulse, the pace capacitor discharges to balance charges across electrodes. The discharge path is typically through low impedance switches and referred to the device ground. The combination of the low impedance switches from the electrodes to the device ground, and over and under voltage protection diodes between each electrode and the device ground causes a high DC rectification current to flow through each electrode where an RF signal is induced (e.g., by an MRI scanner). However, in the present disclosure, a floating or semi-floating discharge is used to effectively increase the impedance seen between the fast discharge electrodes and the device ground, as described in detail herein. This significantly reduces or eliminates any DC rectification current that would otherwise occur due to RF interference during the fast discharge phase.

In the systems and methods described herein, during MRI scanning, a fast discharge configuration is set such that there is a relatively high impedance between a device ground (GND) and electrodes across which the fast discharge is occurring. Two implementations are discussed herein: a floating fast discharge configuration, and a semi-floating fast discharge configuration.

In the semi-floating fast discharge configuration, a high-impedance switch is coupled between the electrodes and the device ground. Rectification current is greatly reduced but still present, and the high-impedance switch guarantees a bias point for nodes in the pacing circuit. The bias point may be needed depending on how switches in the pacing circuit are implemented (e.g., some switches do not operate if a voltage at their terminals is too high). In contrast, in the floating fast discharge configuration, there is no switch to the device ground. This eliminates the RF inducted rectification current. Both the semi-floating fast discharge configuration and the floating fast discharge configuration are described herein in detail.

Figure 2:
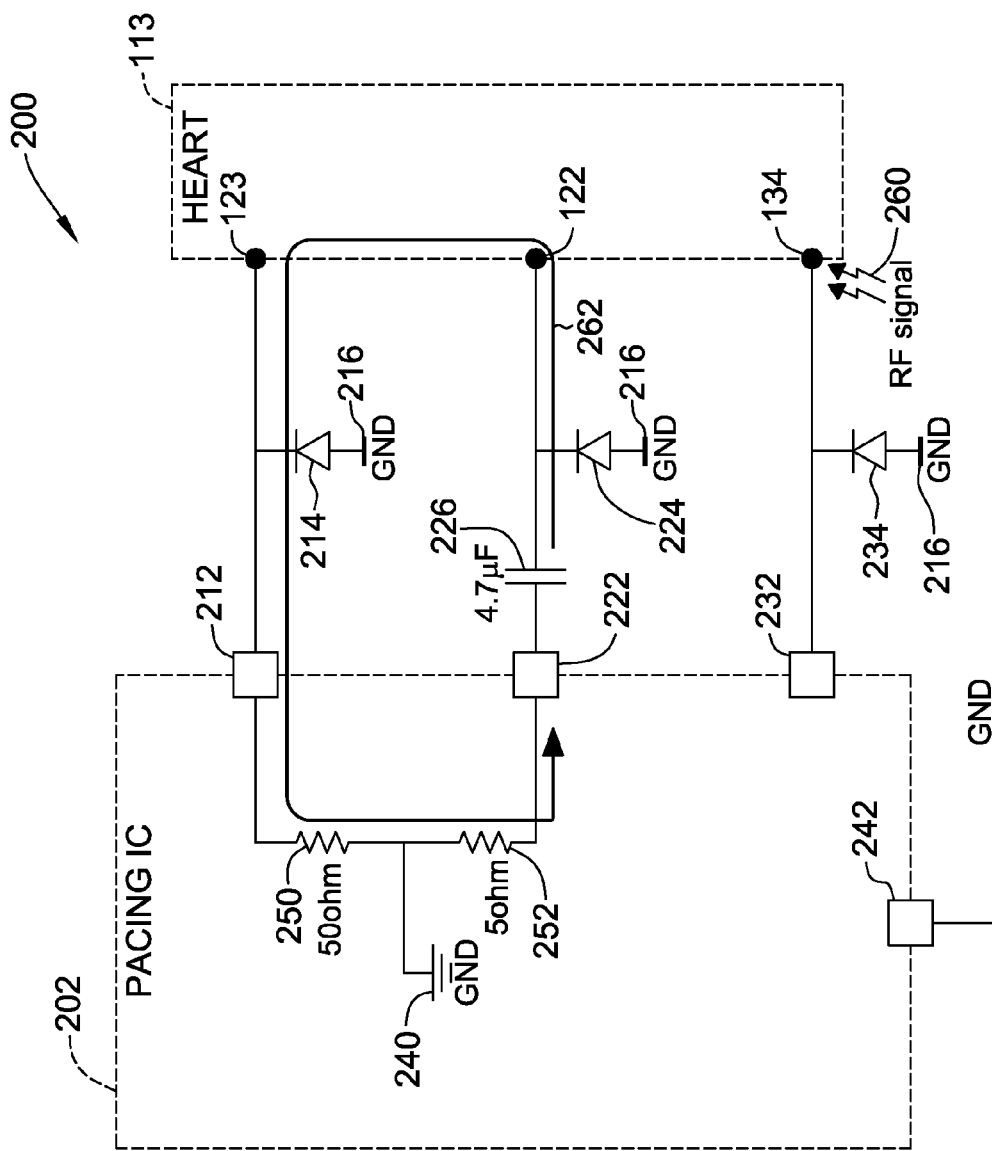
FIG. 2 is a schematic diagram of a known pacing circuit.

FIG. 2 is a schematic diagram of a known pacing circuit 200. Pacing circuit 200 is formed by a pacing integrated circuit (IC) 202, the patient's heart 113, and additional components, as described herein. RA ring electrode 123, RA tip electrode 122, and RV ring electrode 134 are implanted in heart 113.

RA ring electrode 123 is electrically coupled to a first pace output node 212 of pacing IC 202, and a first diode 214 is electrically coupled between RA ring electrode 123 and a ground 216. RA tip electrode 122 is electrically coupled to a pace return node 222 of pacing IC 202, and a second diode 224 is electrically coupled between RA tip electrode 122 and ground 216. Further, a pace capacitor 226 is electrically coupled between RA tip electrode 122 and pace return node 222. RV ring electrode 134 is electrically coupled to a second pace output node 232 of pacing IC 202, and a third diode 234 is electrically coupled between RV ring electrode 134 and ground 216.

Pacing IC 202 includes a ground connection 240 that is connected to ground 216 via a ground node 242 of pacing IC 202. In pacing IC 202, a first resistor 250 is electrically coupled between first pace output node 212 and ground connection 240, and a second resistor 252 is electrically coupled between pace return node 222 and ground connection 240.

As shown in FIG. 2, pacing circuit 200 may be subjected to RF signals 260 (e.g., from an MRI scanner). During a fast discharge phase of pacing circuit 200, a pace capacitor 226 discharges along a discharge current path 262. When RF signal 260 is present during the fast discharge phase, however, a high DC rectification current is generated, which may cause undesirable atrial fibrillation.

Figure 3:
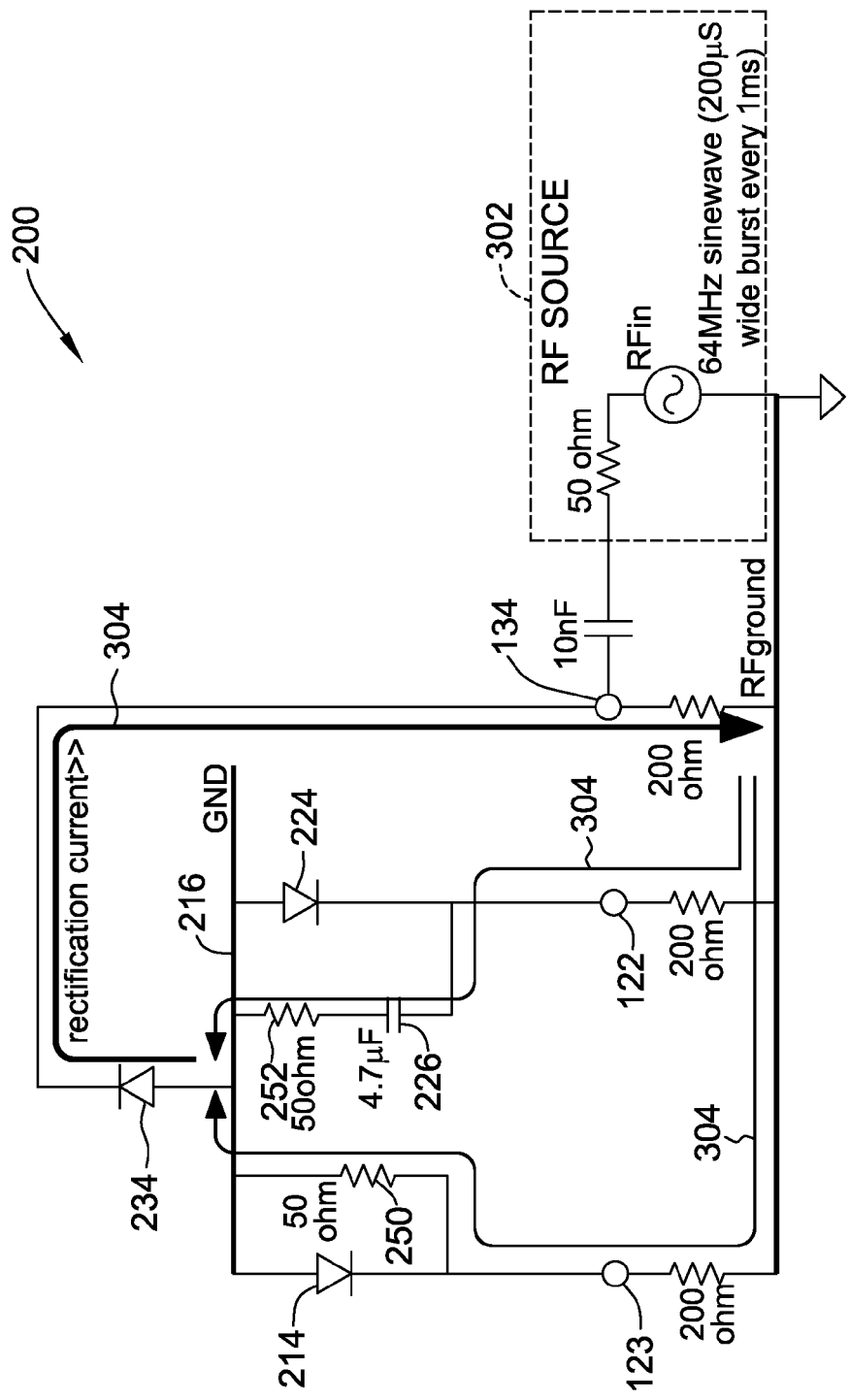
FIG. 3 is a circuit diagram of the known pacing circuit shown in FIG. 2.

FIG. 3 is a circuit diagram of known pacing circuit 200. As shown in FIG. 3, RF signals 260 may be represented by an RF source 302. During fast discharge, RF signals 260 cause a relatively high DC rectification current 304 to be generated (e.g., in the milliamp (mA) range). DC rectification current 304 flows through RV ring electrode 134 and, and subsequently through RA ring electrode 123 and RA tip electrode 122 to ground 216. DC rectification current 304 may cause undesirable atrial fibrillation, as described above. Accordingly, in the systems and methods described herein, a floating or semi-floating fast discharge configuration is used to prevent the generation of a large DC rectification current.

Figure 4:
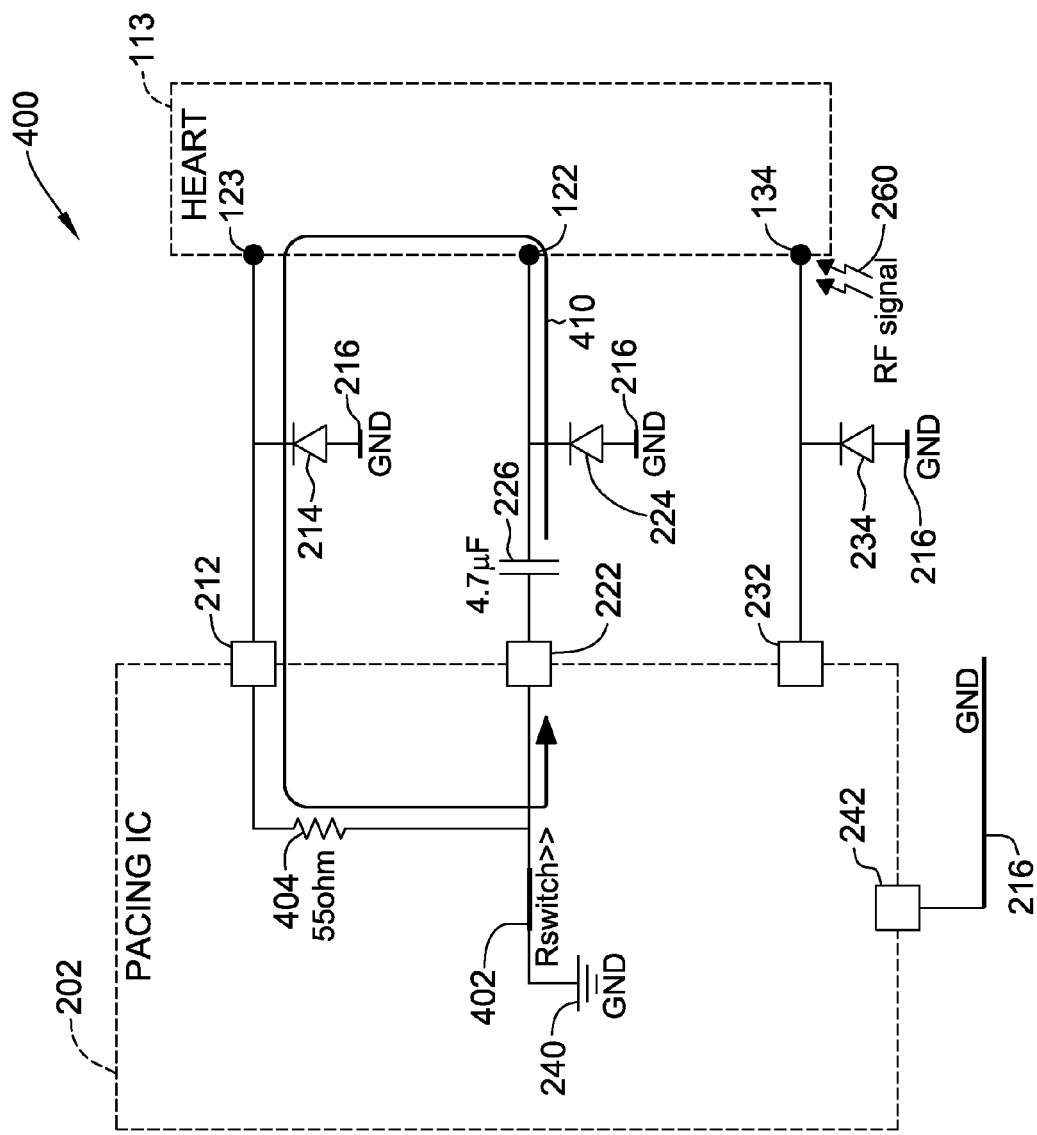
FIG. 4 is a schematic diagram of one embodiment of a pacing circuit that has a semi-floating fast discharge configuration.

FIG. 4 is a schematic diagram of a pacing circuit 400 that includes a semi-floating fast discharge configuration. As shown in FIG. 4, in contrast to pacing circuit 200, pacing circuit 400 includes a high-impedance switch 402 electrically coupled between first pace output node 212 and ground connection 240. High-impedance switch 402 is also electrically coupled between pace return node 222 and ground connection 240. Further, as compared to pacing circuit 200, first and second resistors 250 and 252 are consolidated into a single resistor 404 electrically coupled between first pace output node 212 and high-impedance switch 402. In this embodiment, resistor 404 has a resistance of approximately 55 ohms. Alternatively, resistor 404 may have any suitable resistance.

High-impedance switch 402 has a relatively high impedance. For example, high-impedance switch 402 may have a resistance of greater than approximately 10 kilo-ohms (e.g., tens of kilo-ohms).

As shown in FIG. 4, during a fast discharge phase of pacing circuit 400, pace capacitor 226 discharges along a discharge current path 410, which is similar to discharge current path 262 (shown in FIG. 2). However, a DC rectification current for pacing circuit 400 is significantly different from DC rectification current 304.

Figure 5:
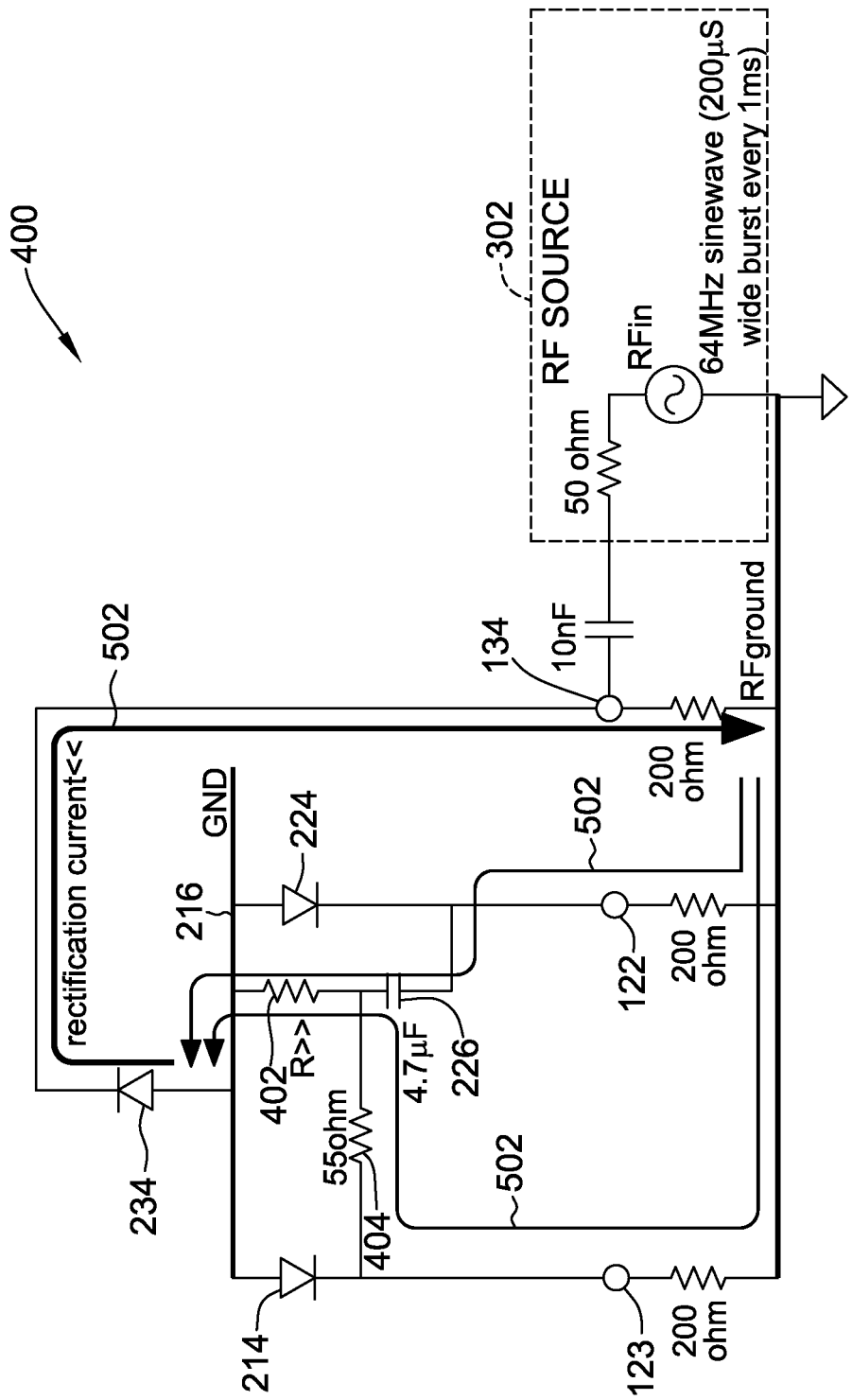
FIG. 5 is a circuit diagram of the pacing circuit shown in FIG. 4.

FIG. 5 is a circuit diagram of pacing circuit 400. As shown in FIG. 5, during fast discharge, RF signal 260 causes a DC rectification current 502 to be generated. Notably, because high-impedance switch 402 having a relatively high impedance is placed in pacing circuit 400, DC rectification current 502 is substantially smaller than DC rectification current 304. For example, DC rectification current 502 may be on the order of microamps (μA).

Figure 6:
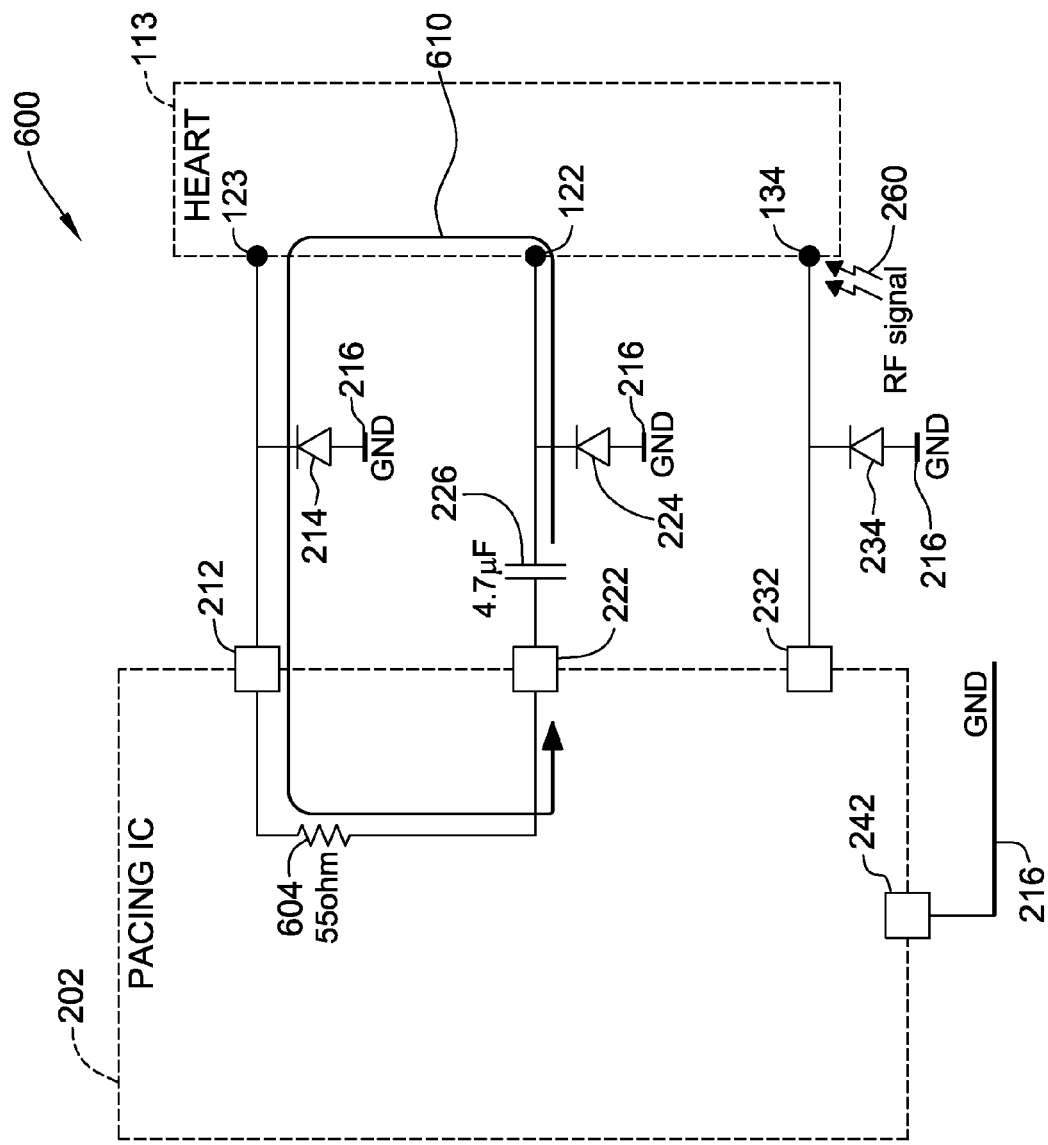
FIG. 6 is a schematic diagram of one embodiment of a pacing circuit that has a floating fast discharge configuration.

FIG. 6 is a schematic diagram of a pacing circuit 600 that includes a floating fast discharge configuration. As shown in FIG. 6, in contrast to pacing circuit 200, there is no connection to ground inside pacing IC 202 for first pace output node 212 and pace return node 222. This can also be thought of as including a high-impedance switch 402 (shown in FIGS. 4 and 5) with an effectively infinite impedance. Further, as compared to pacing circuit 200, first and second resistors 250 and 252 are consolidated into a single resistor 604 electrically coupled between first pace output node 212 and pace return node 222. In this embodiment, resistor 604 has a resistance of approximately 55 ohms. Alternatively, resistor 604 may have any suitable resistance.

As shown in FIG. 6, during a fast discharge phase of pacing circuit 600, pace capacitor 226 discharges along a discharge current path 610, which is similar to discharge current path 262 (shown in FIG. 2).

Figure 7:
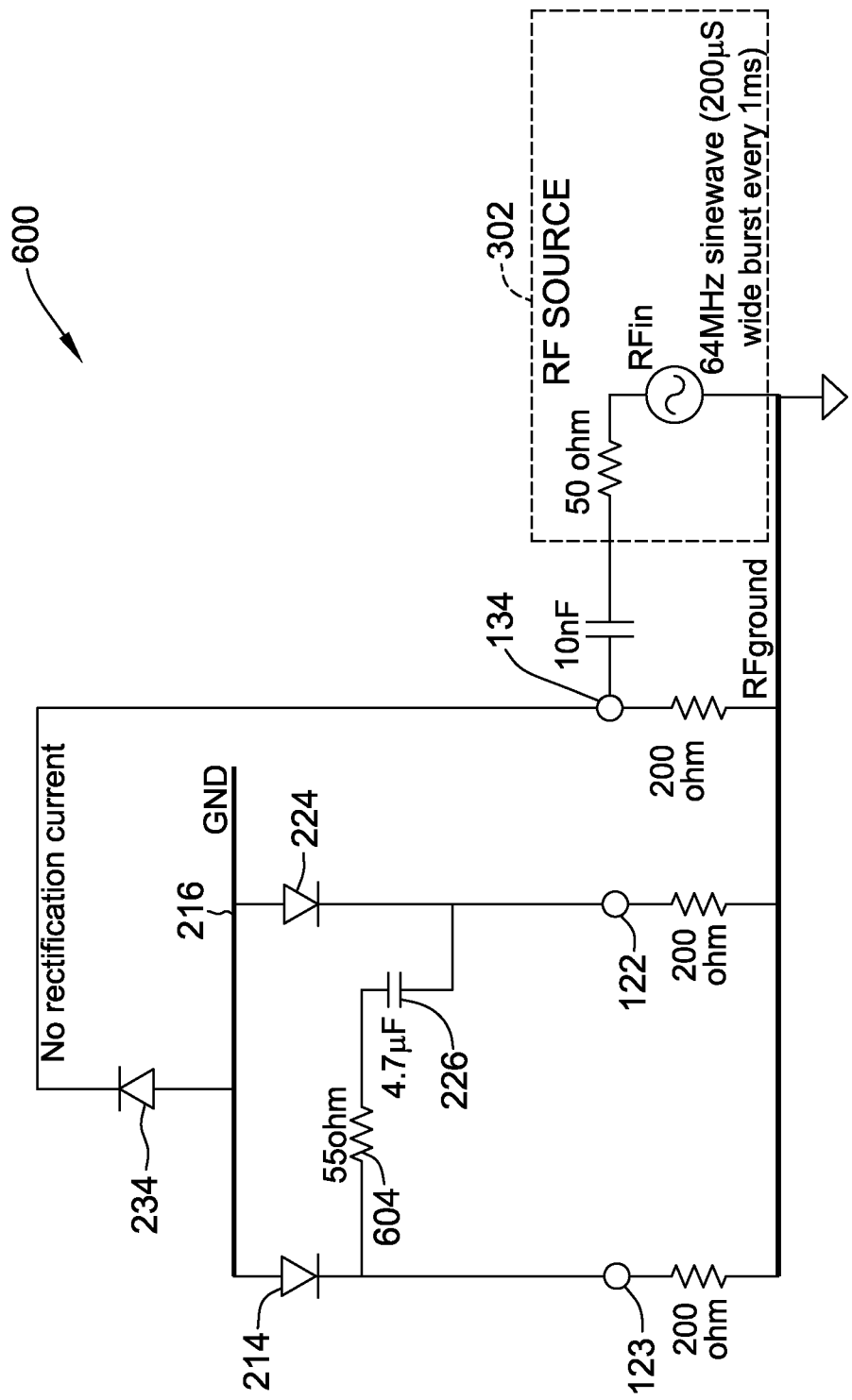
FIG. 7 is a circuit diagram of the pacing circuit shown in FIG. 6.

FIG. 7 is a circuit diagram of pacing circuit 600. As shown in FIG. 7, during fast discharge, no DC rectification current is generated. Specifically, because there is no connection to ground inside pacing IC 202 for first pace output node 212 and pace return node 222, no DC rectification current is generated. Accordingly, a floating fast discharge configuration provides even better protection against generating a DC rectification current than a semi-floating fast discharge configuration. However, as explained above, high-impedance switch 402 of the semi-floating fast discharge configuration guarantees a bias point for first pace output node 212 and pace return node 222.

The systems and methods described herein provide patients with an MRI-compatible pacing device that allows full-body MRI scans to be performed on pacing-dependent patients. The pacing device has a semi-floating or floating fast discharge configuration that prevents generation of a large DC rectification current during RF interference.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:
1. A cardiac pacing system comprising:
a right atrial ring electrode;
a right atrial tip electrode;
a right ventricle ring electrode; and
a pacing integrated circuit (IC) comprising:
a first pace output node electrically coupled to the right atrial ring electrode;
a pace return node electrically coupled to the right atrial tip electrode; and
a second pace output node electrically coupled to the right ventricle ring electrode, wherein there is no switch and no other connection in the pacing IC from the first pace output node to ground, and wherein there is no switch and no other connection in the pacing IC from the pace return node to ground, such that the pacing IC has a floating fast discharge configuration that facilitates eliminating a DC rectification current generated from RF interference during a fast discharge phase.

2. The cardiac pacing system of claim 1, wherein the pacing IC further comprises a single resistor electrically coupled between the first pace output node and the pace return node.

3. The cardiac pacing system of claim 2, wherein the single resistor has a resistance of 55 ohms.

4. The cardiac pacing system of claim 1, wherein the floating fast discharge configuration facilitates eliminating a DC rectification current generated from RF interference generated by an MRI scanner.

5. A cardiac pacing system comprising:
a right atrial ring electrode;
a right atrial tip electrode;
a right ventricle ring electrode; and
a pacing integrated circuit (IC) comprising:
a first pace output node electrically coupled to the right atrial ring electrode;
a pace return node electrically coupled to the right atrial tip electrode; and
a second pace output node electrically coupled to the right ventricle ring electrode,
wherein, in the pacing IC, the first pace output node and the pace return node are connected to ground through a high-impedance switch having a resistance greater than 10 kili-ohms, such that the pacing IC has a semi-floating fast discharge configuration that facilitates reducing a DC rectification current generated from RF interference during a fast discharge phase.

6. The cardiac pacing system of claim 5, wherein the pacing IC further comprises a single resistor electrically coupled between the first pace output node and the pace return node.

7. The cardiac pacing system of claim 6, wherein the single resistor has a resistance of 55 ohms.

8. The cardiac pacing system of claim 5, wherein the semi-floating fast discharge configuration facilitates reducing a DC rectification current generated from RF interference generated by an MRI scanner.

9. A pacing integrated circuit (IC) for use in a cardiac pacing system, the pacing IC comprising:
a first pacing output node configured to be electrically coupled to a right atrial ring electrode;
a pace return node configured to be electrically coupled to a right atrial tip electrode; and
a second pace output node configured to be electrically coupled to a right ventricle ring electrode, wherein, in the pacing IC, the first pace output node and the pace return node are connected to ground through a high-impedance switch having a resistance greater than 10 kili-ohms, such that the pacing IC has a semi-floating fast discharge configuration that facilitates reducing a DC rectification current generated from RF interference during a fast discharge phase.

10. The pacing IC of claim 9, further comprising a single resistor electrically coupled between the first pace output node and the pace return node.

11. The pacing IC of claim 10, wherein the single resistor has a resistance of 55 ohms.

12. The pacing IC of claim 9, wherein the semi-floating fast discharge configuration facilitates reducing a DC rectification current generated from RF interference generated by an MRI scanner.

13. A pacing integrated circuit (IC) for use in a cardiac pacing system, the pacing IC comprising:
a first pacing output node configured to be electrically coupled to a right atrial ring electrode;
a pace return node configured to be electrically coupled to a right atrial tip electrode; and
a second pace output node configured to be electrically coupled to a right ventricle ring electrode, wherein there is no switch and no other connection in the pacing IC from the first pace output node to ground, and wherein there is no switch and no other connection in the pacing IC from the pace return node to ground, such that the pacing IC has a floating fast discharge configuration that facilitates eliminating a DC rectification current generated from RF interference during a fast discharge phase.

14. The pacing IC of claim 13, further comprising a single resistor electrically coupled between the first pace output node and the pace return node.

15. The pacing IC of claim 14, wherein the single resistor has a resistance of 55 ohms.

16. The pacing IC of claim 13, wherein the floating fast discharge configuration facilitates eliminating a DC rectification current generated from RF interference generated by an MRI scanner.

* * * * *